(12) United States Patent
Nahon et al.

(10) Patent No.: US 6,546,932 B1
(45) Date of Patent: Apr. 15, 2003

(54) CRYOGENIC METHOD AND APPARATUS FOR PROMOTING ANGIOGENESIS

(75) Inventors: Daniel Nahon, Ottawa (CA); Mathieu-Philippe Aubert, Saint-Laurent (CA); Philippe Marchand, Hudson (CA); Marwan Abboud, Pierrenfonds (CA); Steven G. Arless, Beaconsfield (CA); Richard Gallo, Ile des Soeurs (CA); Marc Dubuc, Longueuil (CA); Sean Carroll, Beaconsfield (CA); Dan Wittenberger, Pierrenfonds (CA); John W. Lehmann, Wayland, MA (US)

(73) Assignee: CryoCath Technologies Inc., Kirkland (CA)

( * ) Notice: Subject to any disclaimer, the term of this patent is extended or adjusted under 35 U.S.C. 154(b) by 0 days.

(21) Appl. No.: 09/543,108

(22) Filed: Apr. 5, 2000

Related U.S. Application Data
(60) Provisional application No. 60/127,762, filed on Apr. 5, 1999.

(51) Int. Cl.[7] ............................................. A61B 19/00
(52) U.S. Cl. ......................... 128/898; 606/20; 606/21; 606/23; 606/24; 607/104; 607/105; 607/113
(58) Field of Search ................................ 606/20, 21, 22, 606/23, 24, 25, 26; 607/104, 105, 107, 113, 96; 128/898

(56) References Cited

U.S. PATENT DOCUMENTS

| | | | |
|---|---|---|---|
| 5,389,096 A | 2/1995 | Aita et al. | |
| 5,800,488 A | * 9/1998 | Crockett | ...................... 607/105 |
| 5,807,384 A | 9/1998 | Mueller | |
| 5,873,366 A | 2/1999 | Chim et al. | |
| 5,875,782 A | 3/1999 | Ferrari et al. | |
| 5,885,272 A | 3/1999 | Aita et al. | |
| 5,885,276 A | 3/1999 | Ammar et al. | |
| 5,899,898 A | 5/1999 | Arless et al. | .................. 606/22 |
| 5,925,033 A | 7/1999 | Aita et al. | |
| 6,030,380 A | 2/2000 | Auth et al. | |
| 6,032,674 A | 3/2000 | Eggers et al. | |
| 6,080,163 A | 6/2000 | Hussein et al. | ............. 606/108 |

FOREIGN PATENT DOCUMENTS

| | | |
|---|---|---|
| WO | WO 99/52455 | 10/1999 |
| WO | WO 01/37919 | 5/2001 |

\* cited by examiner

*Primary Examiner*—Rosiland S. Kearney
(74) *Attorney, Agent, or Firm*—Christopher & Weisberg, P.A.

(57) ABSTRACT

A method of promoting blood vessel growth includes the steps of providing a cryocatheter having a thermally transmission region; placing the cryocatheter proximate an area of tissue to be treated; cooling the thermally transmissive region of the cryocatheter proximate the area of tissue to a temperature sufficient to injure the area of tissue; allowing the area of tissue to warm; and removing the cryocatheter from the area of tissue. Prior, during or after the cooling step, the area of tissue can be mechanically traumatized, and drugs can be injected into the tissue.

18 Claims, 2 Drawing Sheets

FIG. 9
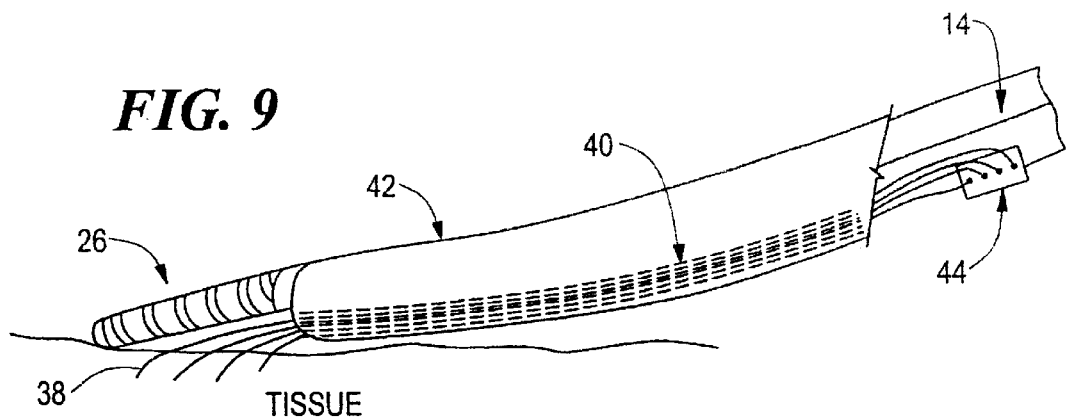
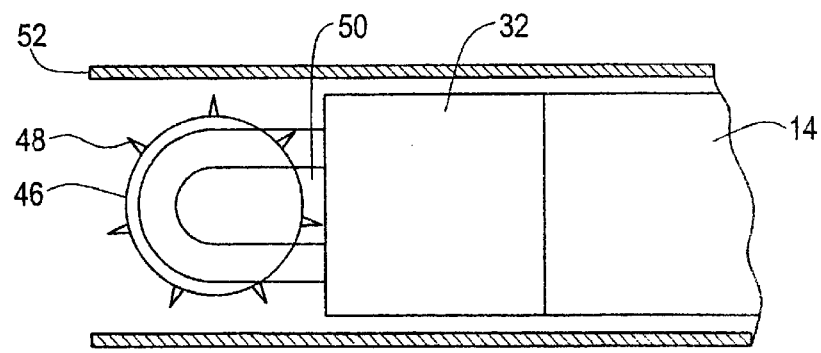
FIG. 10
FIG. 11
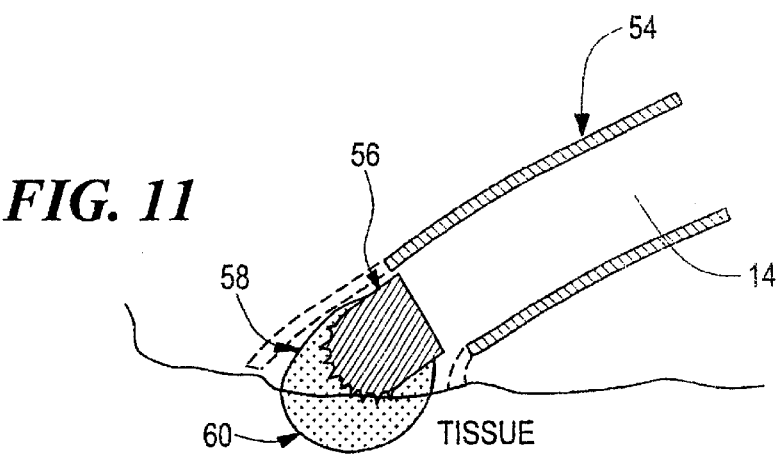

CRYOGENIC METHOD AND APPARATUS FOR PROMOTING ANGIOGENESIS

CROSS-REFERENCE TO RELATED APPLICATIONS

This application claims priority from U.S. Provisional Patent Application Serial No. 60/127,762, filed Apr. 5, 1999.

STATEMENT REGARDING FEDERALLY SPONSORED RESEARCH

Not applicable.

FIELD OF THE INVENTION

This invention relates to vascular growth, and more particularly to apparatus and methods for using extremely cold temperatures to promote angiogenesis.

BACKGROUND OF THE INVENTION

Angiogenesis relates to the formation of blood vessels in living tissue. Not surprisingly, vascular growth or the lack thereof significantly affects living tissue. In adults, the body's network of blood vessels is stable. However, under certain circumstances, such as physical injury, the body causes new blood vessels to grow. Various drug and gene therapies are under study that show promise in amplifying angiogenesis where it naturally occurs, and promoting it where it does not otherwise occur. Drug and gene therapy, however, can not only be difficult to localize, but the mechanisms by which they operate are also poorly understood and may cause unwanted side effects. It would therefore be desirable to provide an alternative method of promoting vascular growth.

SUMMARY OF THE INVENTION

The present invention provides a method of promoting blood vessel growth using extremely cold temperature. The cold temperature is used to create one or more cold affected zones in tissue, wherein the treatment is of a character that injures or traumatizes the tissue enough to provoke an angiogenic response, but yet does not completely kill all of the cells in the cold affected zone. In other words, the present invention seeks to obtain a balance between minimizing trauma to tissue while maximizing angiogenic response.

In an exemplary method, a cryocatheter having a thermally transmissive regon is provided. The cryocatheter is placed proximate an area of tissue to be treated and cooled to a temperature sufficient to traumatize the area of tissue. The tissue can be rewarmed and cooled again one or more times. Prior, during or after tissue cooling the tissue can be mechanically traumatized by the creation of single or multiple pricks, scores, tears or channels.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIGS. 9–11 illustrate alternative tip configuration in association with additional treatment structures.

DETAILED DESCRIPTION OF THE INVENTION

Figure 1:
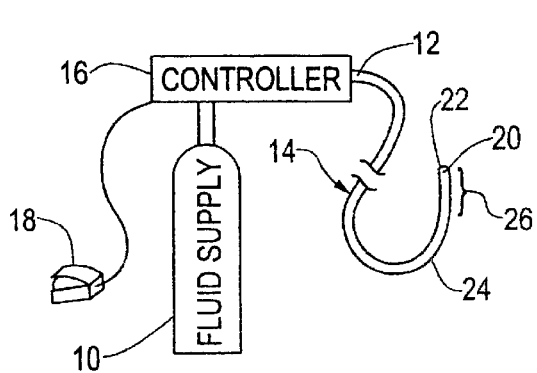
FIG. 1 is a schematic illustration of an embodiment of a cryosurgical system in accordance with the invention.

FIG. 1 is a schematic illustration of a cryosurgical system in accordance with the invention that can be employed as described below to promote angiogenesis. The system includes a supply of cryogenic or cooling fluid 10 in communication with the proximal end 12 of a flexible catheter 14. A fluid controller 16 is interposed or in-line between the cryogenic fluid supply 10 and the catheter 14 for regulating the flow of cryogenic fluid into the catheter in response to a controller command. Controller commands can include programmed instructions, sensor signals, and manual user input. For example, the fluid controller 16 can be programmed or configured to increase and decrease the pressure of the fluid by predetermined pressure increments over predetermined time intervals. In another exemplary embodiment, the fluid controller 16 can be responsive to input from a foot pedal 18 to permit flow of the cryogenic fluid into the catheter 14. One or more temperature sensors 20 in electrical communication with the controller 16 can be provided to regulate or terminate the flow of cryogenic fluid into the catheter 14 when a predetermined temperature at a selected point or points on or within the catheter is/are obtained. For example a temperature sensor can be placed at a point proximate the distal end 22 of the catheter and other temperature sensors 20 can be placed at spaced intervals between the distal end of the catheter and another point that is between the distal end and the proximal end. The cryogenic fluid can be in a liquid or a gas state.

An extremely low temperature can be achieved within the catheter, and more particularly on the surface of the catheter by cooling the fluid to a predetermined temperature prior to its introduction into the catheter, by allowing a liquid state cryogenic fluid to boil or vaporize, or by allowing a gas state cryogenic fluid to expand. Exemplary liquids include chlorodifluoromethane, polydimethylsiloxane, ethyl alcohol, HFC's such as AZ-20 (a 50-50 mixture of difluoromethane & pentafluoroethane sold by Allied Signal), and CFC's such as DuPont's Freon. Exemplary gasses include nitrous oxide, and carbon dioxide.

The catheter 14 includes a flexible member 24 having a thermally-transmissive region 26 and a fluid path through the flexible member to the thermally-transmissive region. A fluid path is also provided from the thermally-transmissive region to a point external to the catheter, such as the proximal end 12. Although described in greater detail below, exemplary fluid paths can be one or more channels defined by the flexible member 24, and/or by one or more additional flexible members that are internal to the first flexible member 24. Also, even though many materials and structures can be thermally conductive or thermally transmissive if chilled to a very low temperature and/or cold soaked, as used herein, a "thermally-transmissive region" is intended to broadly encompass any structure or region of the catheter 14 that readily conducts heat. For example, a metal structure exposed (directly or indirectly) to the cryogenic fluid path is considered a thermally-transmissive region 26 even if an adjacent polymeric or latex catheter portion also permits heat transfer, but to a much lesser extent than the metal. Thus, the thermally-transmissive region 26 can be viewed as a relative term to compare the heat transfer characteristics of different catheter regions or structures. A thermally-transmissive region or element is not intended to encompass a structure that is excited by RF or other energy source to a point where it begins to radiate heat, for example.

Furthermore, while the thermally-transmissive region 26 can include a single, continuous, and uninterrupted surface or structure, it can also include multiple, discrete, thermallytransmissive structures that collectively define a thermally-transmissive region that is elongate or linear. Alternatively, the thermally-transmissive region can be at a single focal location, such as the distal tip of the catheter. Additional details of the thermally-transmissive region 26 and the thermal transfer process are described in greater detail below.

In exemplary embodiments of the invention, the thermally-transmissive region 26 of the catheter 14 is deformable. An exemplary deformation is from a linear configuration to an arcuate configuration and is accomplished using mechanical and/or electrical devices known to those skilled in the art. For example, a wall portion of the flexible member 24 can include a metal braid to make the catheter torqueable for overall catheter steering and placement. Additionally, a wire or cable can be incorporated with, or inserted into, the catheter for deformation of the thermally transmissive region 26.

Figure 2:
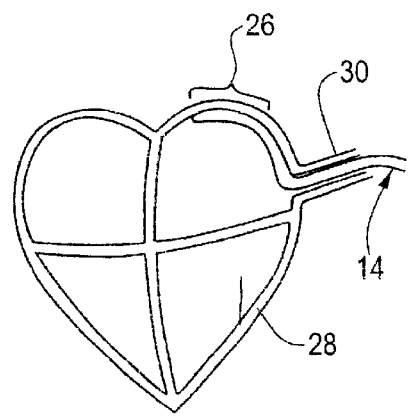
FIG. 2 is a sectional view of a heart muscle showing placement of the catheter of FIG. 1.

The cryogenic system of FIG. 1 is better understood with reference to its use in an operative procedure as shown in FIG. 2. Following the determination of a proposed treatment site within a heart muscle 28 for example, the catheter 14 is directed through a blood vessel 30 to a region within the heart. The thermally-transmissive region 26 is placed proximate to the tissue to be treated. The thermally-transmissive region of the catheter may be deformed to conform to the curvature of the tissue before, during, or after placement against the tissue. The controller 16 allows or causes cryogenic fluid to flow from the cryogenic fluid supply 10 to the fluid path in the catheter 14 and thence to the thermally-transmissive region 26 to treat the desired area. In one embodiment a first conduit is concentric within a second conduit and cooling fluid travels to a thermally-transmissive region proximate a closed distal end of the catheter through a first conduit (fluid path) and is exhausted from the catheter through the second conduit (fluid path).

Figure 3:
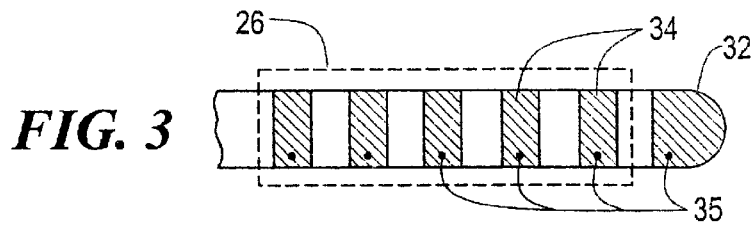
FIG. 3 illustrates the tip region of one embodiment of the catheter in accordance with the invention.

Referring specifically to the embodiment depicted in FIG. 3, multiple thermallytransmissive elements 34 are integral with a distal portion of a catheter having a thermally transmissive tip 32. Thermocouples 35 can be associated with one or more of the elements 34 and the tip 32. Additional details of cryocatheter construction are found in U.S. Pat. Nos. 5,899,898 and 5,899,899 to Arless, which are incorporated herein by reference.

Figure 4:
FIGS. 4–8 illustrate alternative tip configurations for cyro-angiogenic treatment.
Figure 5:
Figure 6:
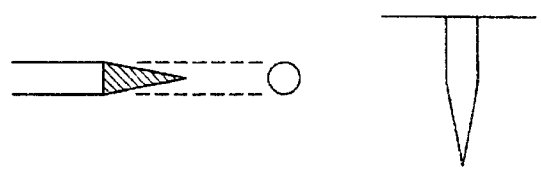
Figure 7:
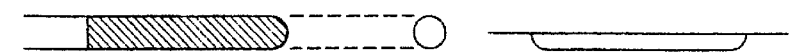
Figure 8:
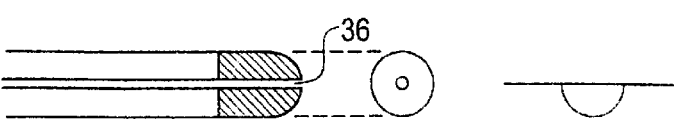

FIGS. 4–8 illustrate alternative embodiments of the thermally transmissive region 26. To the right of each drawing is an illustration of the general shape of the region treated by each embodiment as seen in plan view and as seen in cross-section. More specifically, FIG. 4 depicts a rounded tip, such as element 32 of FIG. 3. FIG. 5 shows a flat, paddle-like tip; and FIG. 6 shows a needle tip suitable for penetrating tissue. FIG. 7 illustrates a non-segmented linear tip. FIG. 8 shows a tip with a separate channel 36 within the tip or beside it to inject drugs directly in the tissue, such as vascular endothelial growth factor (VEGF), before, during or after cooling tissue as described below. The drug(s) can be deposited on the surface of the tissue for injected into the tissue.

Angiogenesis can be promoted in selected tissue with the above described devices by injuring tissue over a selected area. For example, to treat ischemia, a cryocatheter as described above, is placed on the heart tissue to be treated. The cooling or thermally transmissive region 26 of the catheter is chilled to a temperature of −20° C. to −80° C. for five seconds to five minutes and then allowed to warm or thaw to a temperature in the range of 0° C. to body temperature. This step is then repeated one or more times. In an exemplary procedure, four or more three or more injuries are made tissue at regular intervals 5–15 mm apart, wherein the tissue is injured to a depth of about 3.0 mm or more to provide a relatively wide and deep treated tissue zone. Treatment zone geometry can be varied widely by varying pip geometry, using tips such as shown in FIGS. 4–8, as well as by varying freeze rate, thaw rate, freeze time, and ultimate temperature. A greater or fewer number of treatment zones can be created as desired to stimulate a greater or lesser area. Freezing the tissue initiates an inflamnnatory response which triggers an angiogenic process, leading to new blood vessel growth. However, the ability to dose the injury minimizes tissue necrosis while maximizing angiogenic response.

Another way to minimize tissue damage, but to trigger an angiogenic reaction, is to apply high frequency electrical or microwave energy to the tissue while cooling the catheter/tissue interface with a cryogenic fluid alternative method. Engineered The depth to which tissue is injured can be a significant factor in promoting angiogenesis. Thus, FIG. 9 depicts a cryocatheter 14 with supplemental structures that can increase injury depth, such as one or more thermally conductive wires, needle or stylets 38. In an exemplary embodiment the stylets 38 are stainless steel wires less than 0.050 inches in diameter. Although the stylets 38 can be integrated with the catheter 14, they can be independent therefrom. For example, FIG. 9 shows a cryocatheter 14 disposed within a guide lumen 40 that is part of a shaft portion 42 of the catheter 14. The stylets 38 are disposed within the guide lumen 40 and are axially movable therein. A control mechanism 44 is provided at the proximal end of the catheter that allows the stylets to be advanced and/or retracted individually or in unison.

In an exemplary procedure, the catheter 14 is guided to an area of tissue to be treated. Then the one or more stylets 38 are advanced so as to penetrate the tissue to a selected depth. The catheter 14 is cooled, as described above, and one or more iceballs form on and near the tissue that is proximate the thermally transmissive region 26. The stylets 38, which are in or exposed to the one or more iceballs, conduct cold/remove heat from a region of tissue well below the surface.

Regarding the procedure described with respect to FIG. 9, it should be noted that not only is a deep region of tissue traumatized by extremely cold temperature, but the tissue is also mechanically traumatized by the stylets 38. The combination of trauma mechanisms is believed to be especially effective in promoting angiogenesis.

Another combined trauma device is shown in FIG. 10, wherein a rotatable, ball, wheel or cylinder 46 is secured to the tip 32 of the catheter 14. The cylinder 46 is provided with sharp or rough surface features, such as spikes 48. A thermally conductive support structure 50 conducts heat/cold from the tip 32 to the spikes 48. An introducer/guide catheter 52 is provided to assist with catheter placement. Thus, in an exemplary procedure, the catheter is positioned near tissue as described above, and the tip 32 is cooled. The cold is conducted to the cylinder 46 and to the spikes 48 and thence to the tissue against which the cylinder is pressed and rotated. In alternative procedures, the tissue is traumatized before or after a cooling cycle, or between cool/thaw/cool cycles. Thus, angiogenesis is stimulated by physical and temperature trauma.

Yet another way of providing combination trauma is described with respect to FIG. 11, wherein a catheter 14 is shown within a guide sheath 54, and is slidable therein. The catheter 14 includes a roughened cooling tip 56. In an exemplary procedure using this catheter, the catheter is placed and the tip is cooled to create an iceball 58. After a region of tissue 60 has frozen and has become part of or joined to the iceball 58, the catheter tip 56 is pulled away from the tissue, thereby tearing the region of tissue 60 from the remaining tissue. The roughness of the tip 56 helps to prevent the iceball from separating from the catheter when the catheter is pulled away from the tissue. The sheath 54 can be pushed against the tissue during treatment to shield the tip from surrounding tissue, to help localize the thermal treatment, and to help detach the iceball/frozen tissue from the non-frozen tissue.

A variety of modifications and variations of the present invention are possible in light of the above teachings. It is therefore understood that, within the scope of the appended claims, the present invention may be practiced otherwise than as specifically described hereinabove. All references cited herein are expressly incorporated by reference in their entirety.

What is claimed is:

1. A method of promoting blood vessel growth comprising the steps of:

providing a flexible catheter having a thermally transmissive region;

placing the catheter proximate an area of tissue to be treated without injuring the area of tissue;

cooling the thermally transmissive region of the catheter proximate the area of tissue to a temperature sufficient to trigger an angiogenic response in said area of tissue;

cooling a portion of the area of tissue to a temperature in the range of −20° C. to −80° C. for a duration of five seconds to five minutes, without penetrating the area of tissue;

allowing the area of tissue to warm; and removing the catheter from the area of tissue.

2. The method of claim 1, further comprising the step of cooling the area of tissue a second time to a temperature sufficient to trigger an angiogenic response in said area of tissue after the area of tissue has been allowed to warm.

3. The method of claim 1, wherein the step of cooling includes the step of applying cooling for a time and temperature combination that causes the area of tissue to be frozen to a depth of at least three millimeters.

4. The method of claim 1, wherein the step of cooling includes the step of applying cooling at a rate slower than 4° C. per second.

5. The method of claim 1, wherein the step of allowing the area of tissue to warm includes the step of warming the tissue at a rate faster than 0.5° C. per second.

6. The method of claim 1, further comprising the steps of moving the catheter to a second area of tissue proximate the first area of tissue and cooling the second area of tissue to a temperature sufficient to trigger an angiogenic response in said second area of tissue.

7. The method of claim 6, further comprising the steps of cooling the first and second areas of tissue along a substantially linear path to provide a first linear tissue injury and a second linear tissue injury.

8. The method of claim 7, wherein the first linear path is substantially parallel to the second linear path.

9. The method of claim 1, further comprising the step of selecting a catheter tip having a configuration selected from the group consisting of a rounded tip, a flat-paddle-like tip, a linear tip, and a tip further comprising a channel for injection of fluid.

10. The method of claim 1, further comprising the step of mechanically traumatizing the area of tissue after cooling it.

11. The method of claim 1, further comprising the steps of:

providing a plurality of stylets; and imbedding the plurality of stylets into the area of tissue to be treated at one or more points near the thermally transmissive region of the catheter.

12. The method of claim 1, further comprising the steps of:

providing a thermally transmissive region that has a surface adapted to promote adhesion to ice;

cooling the area of tissue to a temperature that causes an iceball to form that extends from the surface of the thermally transmissive region to a point below the surface of the area of tissue; and pulling the iceball away from the area of tissue, and removing a portion of said area of tissue.

13. A method of promoting blood vessel growth comprising the steps of:

providing a flexible catheter having a thermally transmissive region;

placing the catheter proximate an area of tissue to be treated without injuring the area of tissue;

cooling the thermally transmissive region of the catheter proximate the area of tissue to a temperature sufficient to trigger an angiogenic response in said area of tissue, without penetrating the area of tissue;

allowing the area of tissue to warm;

removing the catheter from the area of tissue; and depositing a drug that promotes angiogenesis on the area of tissue.

14. The method of claim 13, wherein the step of depositing a drug includes the step of injecting a drug that promotes angiogenesis into the area of tissue.

15. The method of claim 13, wherein the drug includes vascular endothelial growth factor.

16. The method of claim 13, wherein the step of depositing a drug that promotes angiogenesis on the area of tissue is in part performed prior to the step of cooling.

17. The method of claim 13, wherein the step of depositing a drug that promotes angiogenesis on the area of tissue is in part performed during the step of cooling.

18. The method of claim 13, wherein the step of depositing a drug that promotes angiogenesis on the area of tissue is in part performed after the step of cooling.

* * * * *